(12) United States Patent
Fischer et al.

(10) Patent No.: US 7,828,135 B2
(45) Date of Patent: Nov. 9, 2010

(54) DEVICE FOR FEEDING STERILE CLOSURES, WHICH ARE DELIVERED IN BAGS, INTO A FILLING SYSTEM FOR BOTTLES OR THE LIKE

(75) Inventors: Sven Fischer, Obertraubling (DE); Oliver Martini, Regensburg (DE)

(73) Assignee: Krones AG, Neutraubling (DE)

( * ) Notice: Subject to any disclaimer, the term of this patent is extended or adjusted under 35 U.S.C. 154(b) by 139 days.

(21) Appl. No.: 11/884,513

(22) PCT Filed: Jan. 19, 2006

(86) PCT No.: PCT/EP2006/000434

§ 371 (c)(1),
(2), (4) Date: Jul. 30, 2008

(87) PCT Pub. No.: WO2006/089603

PCT Pub. Date: Aug. 31, 2006

(65) Prior Publication Data

US 2009/0173602 A1 Jul. 9, 2009

(30) Foreign Application Priority Data

Feb. 22, 2005 (DE) .................. 20 2005 002 903 U

(51) Int. Cl.
*B65B 55/02* (2006.01)
*B67B 1/03* (2006.01)

(52) U.S. Cl. .................. 198/678.1; 198/679; 198/805; 198/465.4

(58) Field of Classification Search ............... 198/465.1, 198/465.4, 582, 619, 678.1, 679, 805; 53/425, 53/426
See application file for complete search history.

(56) References Cited

U.S. PATENT DOCUMENTS

| 2,824,638 | A | * | 2/1958 | De Burgh | 198/619 |
| 5,573,101 | A | * | 11/1996 | Ouwejan | 198/349 |
| 5,664,659 | A | * | 9/1997 | Gaertner | 198/360 |
| 5,819,906 | A | * | 10/1998 | Enderlein et al. | 198/687.1 |
| 5,857,556 | A | * | 1/1999 | Bonacorsi | 198/683 |
| 5,890,583 | A | * | 4/1999 | Garbagnati | 198/805 |
| 6,155,406 | A | * | 12/2000 | Garbagnati | 198/805 |
| 6,357,574 | B1 | * | 3/2002 | Eberle et al. | 198/465.4 |
| 6,460,685 | B1 | * | 10/2002 | Johansson et al. | 198/465.4 |
| 6,991,090 | B2 | * | 1/2006 | Gaertner | 198/680 |
| 7,051,866 | B2 | * | 5/2006 | Irish | 198/681 |
| 7,080,727 | B1 | * | 7/2006 | Sanderson | 198/680 |
| 7,270,228 | B2 | * | 9/2007 | Golias | 198/465.4 |

FOREIGN PATENT DOCUMENTS

| DE | 1 460 621 | 8/1969 |
| DE | 1460621 | 8/1969 |
| DE | 3423436 | 1/1986 |

OTHER PUBLICATIONS

English translation of DE 1 460 621 (16 pages).

* cited by examiner

*Primary Examiner*—Douglas A Hess
(74) *Attorney, Agent, or Firm*—Marshall, Gerstein & Borun LLP

(57) ABSTRACT

A device for feeding sterile closures, which have been delivered in bags, into a filling system for containers, such as bottles, having a housing that features an inlet opening for the bags, an outlet opening for the closures and a sterilization device, wherein a conveying device that transports the bags is provided in the housing, and wherein the conveying device for the bags is embodied as a suspended conveyer.

11 Claims, 4 Drawing Sheets

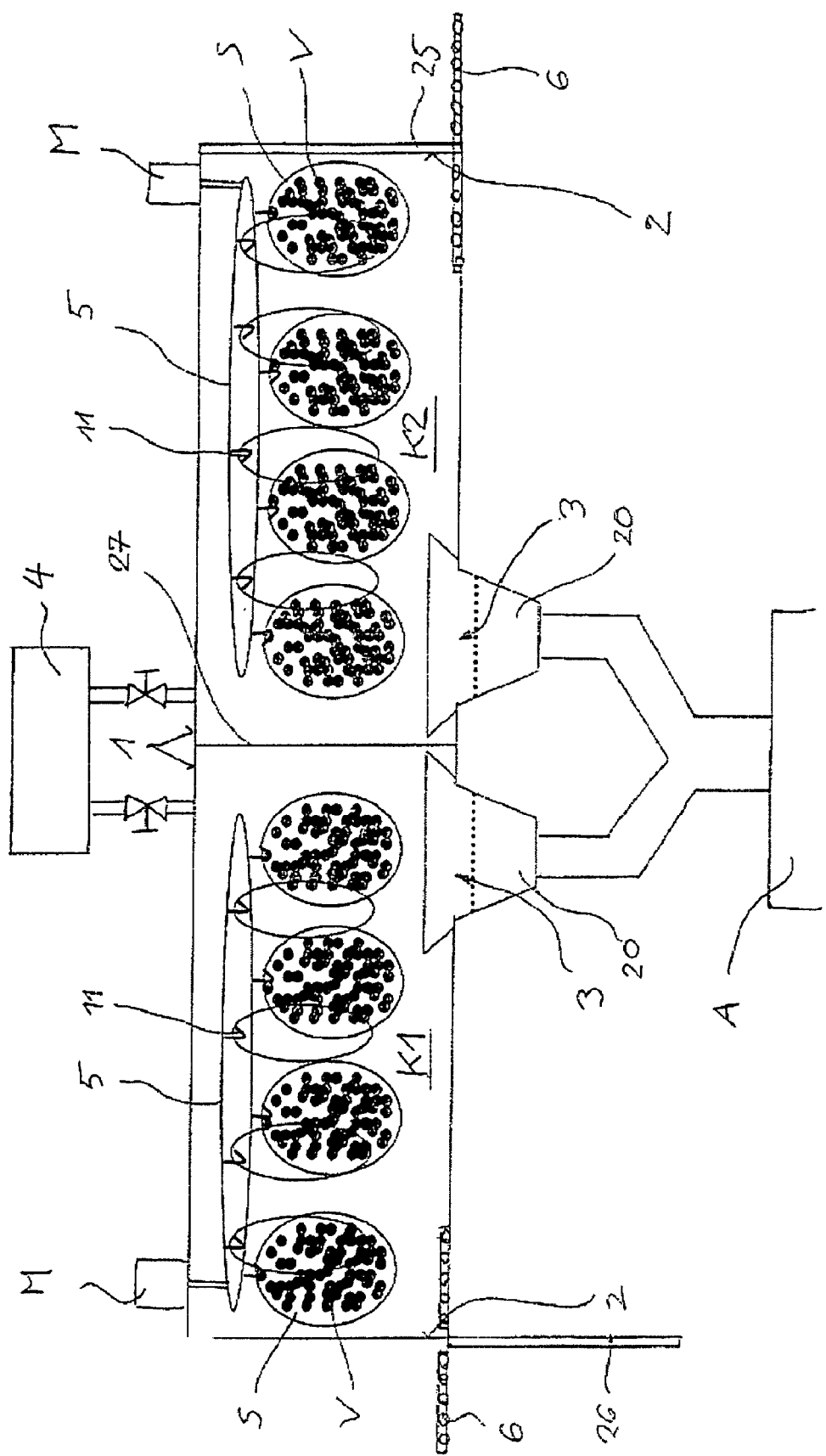

DEVICE FOR FEEDING STERILE CLOSURES, WHICH ARE DELIVERED IN BAGS, INTO A FILLING SYSTEM FOR BOTTLES OR THE LIKE

CROSS-REFERENCE TO RELATED APPLICATION

The present application claims the benefit of priority of International Patent Application No. PCT/EP2006/000434 filed on Jan. 19, 2006, which application claims priority of German Patent Application No. 20 2005 002 903.3 filed Feb. 22, 2005. The entire text of the priority application is incorporated herein by reference in its entirety.

FIELD OF THE DISCLOSURE

The disclosure relates to a device for feeding sterile closures, particularly in bottling operations.

BACKGROUND OF THE DISCLOSURE

Such a device is already in use, with which the conveying device is embodied as a modular conveyor belt, upon which the bags are seated.

With this known device, it is not possible to completely sterilize the bags, given that their exterior surface is partially covered by the modular conveyor belt. Therefore, it cannot be ruled out that, after opening the bags within the housing, the removed closures are reinfected by the germs brought in with the bags.

SUMMARY OF THE DISCLOSURE

The disclosure underlies the task of, with simple methods, reliably preventing a reinfection of the closures after the opening of the bags for a type of device specified above.

According to the disclosure, such task is solved by the fact that the conveying device for the bags is embodied as a suspended conveyer.

In this manner, the exterior surface of the bags is, in practice, completely accessible and can be completely disinfected within the sterilization device. Therefore, a reinfection of the closures before passing the outlet opening into the filling system is impossible.

A particularly advantageous feature is the magnetic propulsion of the suspended conveyer through the drive means attached to the outside of the housing. Thereby, a particularly simple sealing of the housing is possible and the areas of the suspended conveyer rotating in the housing will always remain sterile.

BRIEF DESCRIPTION OF THE DISCLOSURE

In the following, an embodiment of the disclosure is described on the basis of the designs.

Figure 1:
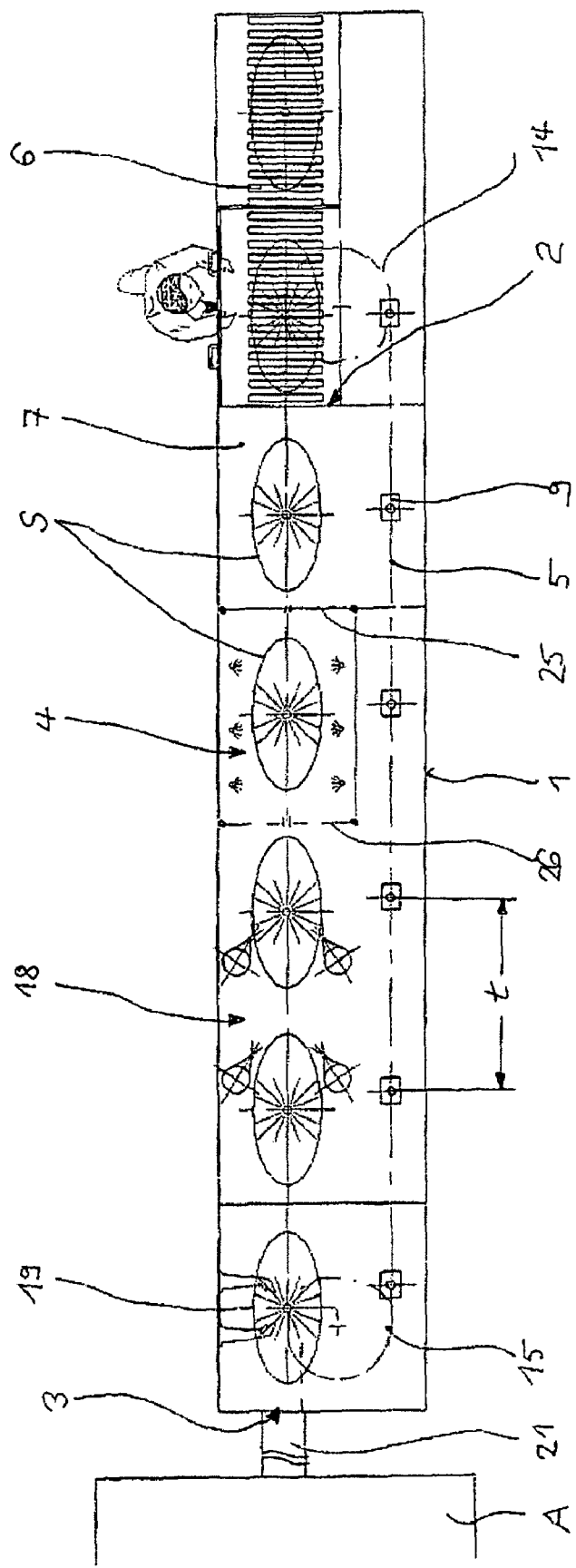

It shows:

FIG. 1 the schematic top view on a device for feeding closures

Figure 2:
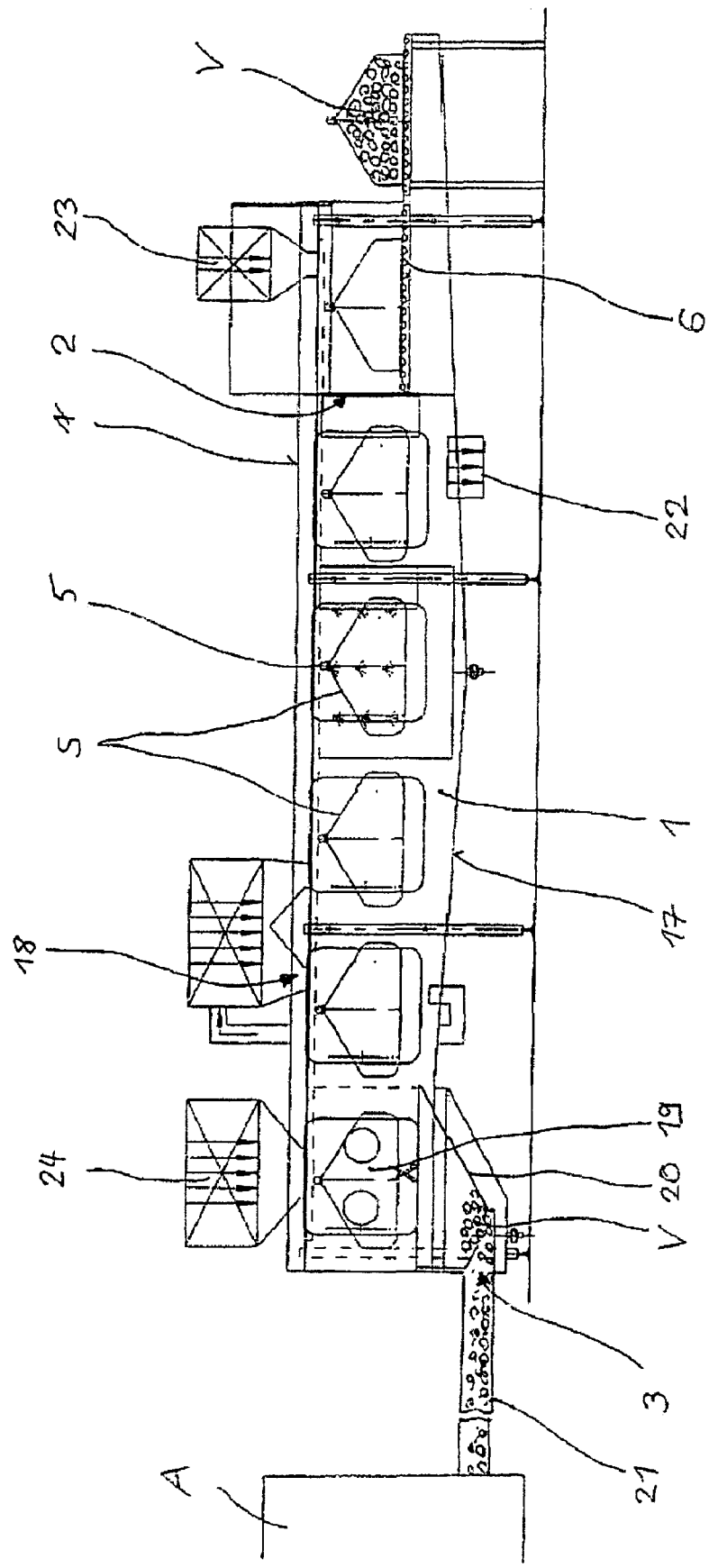

FIG. 2 the side view of the device under FIG. 1

Figure 3:
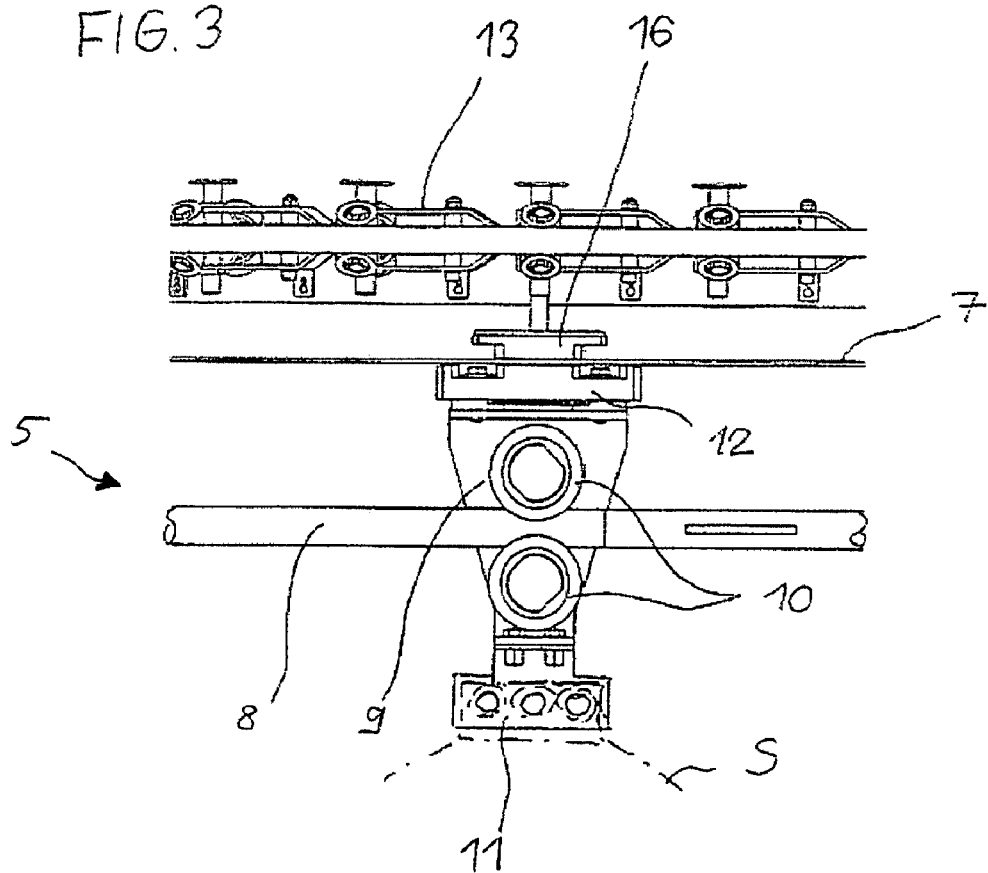

FIG. 3 the enlarged side view of a part of the suspended conveyer

Figure 4:
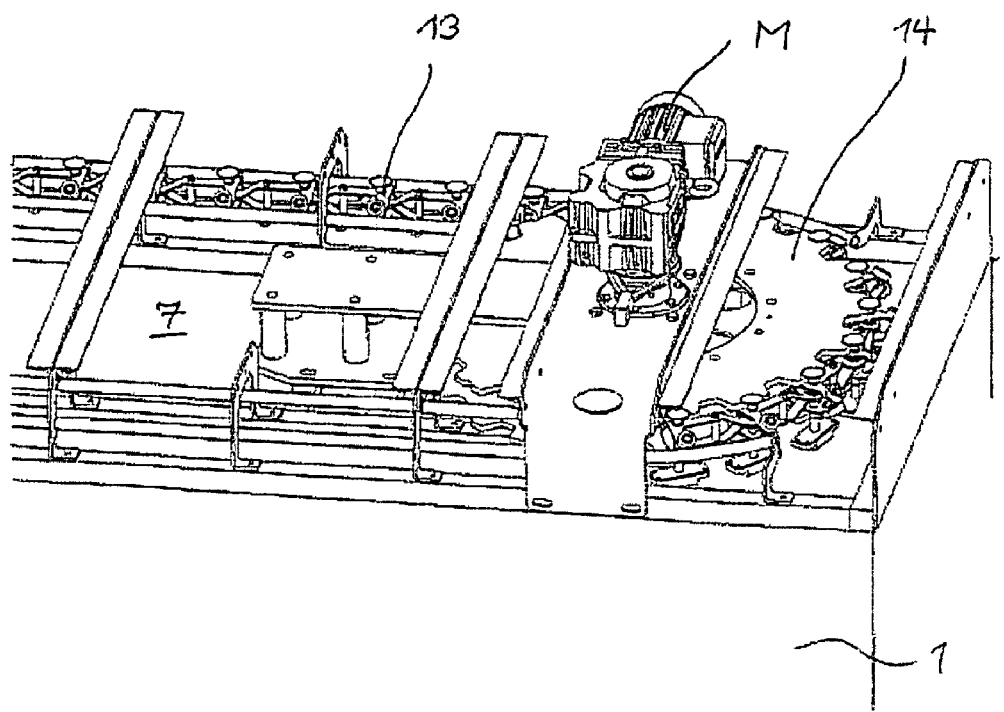

FIG. 4 the enlarged top view on the housing of the device under FIGS. 1 to 3

FIG. 5 the schematic side view of a device with two suspended conveyers and two sterilization chambers.

DETAILED DESCRIPTION OF THE DISCLOSURE

The device under FIGS. 1 to 4 is equipped for inserting closures V, which have been delivered in bags S, into a filling system A for the sterile filling of bottles with a beverage. Preferably, they are reclosable drinking closures (Sportcap). Such drinking closures contain cavities that are accessible with a certain degree of difficulty; such cavities cannot be sufficiently disinfected with normal sterilization in an immersion bath or the like. Therefore, it is customary to provide gas-tight packages for and sterilize such drinking closures by means of gamma radiation in flexible bags made of plastic foil. The use of double bags, the exteriors of which absorb the major contamination during transportation, is also customary.

The device features an oblong housing 1 with an essentially rectangular cross section, the right front side of which embodies an inlet opening 2 for the closed bags S and the opposite front side of which embodies an outlet opening 3 for the sterile closures V, which are removed from the bags S. At the inlet opening 2, a short roll conveyor 6 is provided, which lies partly within and partly outside of the housing 2. The manual insertion of the bags S into the housing is thereby facilitated.

On the top side of the housing 1 (more specifically, its horizontal cover plate 7), a suspended conveyer 5 is attached for the bags S. The suspended conveyer 5 features an oval guide bar 8 that is attached to the inner and/or bottom side of the cover plate 7, on which several individual runners 9 are adjustably guided by means of rollers 10. On its bottom side, each runner 9 has a seating 11 for the suspended transport of each bag S; for example, a hook (FIG. 5) or several horizontal pins (FIG. 3).

On the top side of each runner 9, a permanent magnet 12 is attached, which lies just below the cover plate 7.

On the top and/or exterior of the cover plate 7, an endless link chain 13 that covers the guide bar 8 is housed with two redirecting wheels 14, 15, which is provided with the permanent magnet 16. These lie closely over the cover plate 7 and correspond to the permanent magnet 12 of runner 9. Thus, upon a circulation of the link chain 13 in the direction of the arrow under FIG. 1, the runner 9 is carried forward by magnetic force. The propulsion of the link chain 13 takes place through a motor M, which affects one of the redirecting wheels 15.

It is preferable that the motor M is intermittently operated and steered either automatically or manually, wherein, for each power stroke in singular or multiple strokes, the link chain 13 covers the distance t between two runners 9. The distance t is somewhat greater than the maximum width of a bag S.

As with the runner 9, the link chain 13 can be guided by means of rollers (not shown) on a guide bar (not shown). It can also feature several permanent magnets 16, as runners 9 are present, wherein the distance between the runners 9 can be varied.

In FIG. 1, the actual work stations of the device are provided in the rotating area of the runner 9 in the direction of right to left; i.e., from the inlet opening 2 to the outlet opening 3.

As a first step, a bag comes to the inlet opening 2 of the sterilization device 4 with a distance of at least on bag width. In this, the particular bag S is intensively sprayed with an aqueous peracetic acid solution from all sides by means of several nozzles. Below the sterilization device 4, a catch pan 17 is provided for the sterilization solution, which preferably extends over the entire length of the housing 1.

As a next step, there is a drying device 18 in which the particular bag S is intensively subjected to warm sterile air from several nozzles on all sides.

Finally, the removal device 19 follows at the end of the housing 1, which includes two flexible glove contacts for the operator, so that such operator, with a suitable tool, can cut the bags S open at the bottom end. The removal device 19 further includes a funnel 20 for the closures V falling out of the bags S, which deposits such closures on a vibrating conveyer 21 or the like. This is closed on all sides and guides the closures to the fully housed filling system A.

In the area between the inlet opening 2 and the sterilization device 4, a suction device 22 is housed, in order to prevent the escape of atmospheric fumes that were used for sterilization. Furthermore, a device 23, 24 for injecting sterile air is provided in each area of the inlet opening 2 and each area of the outlet opening 3, in order to reliably prevent the incidence of contaminated ambient air in the housing.

For the improved sealing of the sterilization device 4, it can be provided with an air lock 25, 26 in each inlet and/or outlet. In the most simple case, each airlock exists in one or two folding doors, which are opened by the bag S and closed afterwards by means of spring action.

In FIG. 1, the opened and emptied bags S run in the direction of the rotating area from left to right (i.e., from the outlet opening 3 to the inlet opening 2) and back to the inlet opening 2 and are removed there from the seatings by the operator and are replaced by a full bag S.

If the closures V are delivered in so-called "double bags" S, then the outside bag is briefly removed before hanging the inner bags S on the seatings 11. In this manner, coarse contamination that arrives in the device from the transportation is prevented, so that only the already very pure and/or germ-poor inner bag must be sterilized.

For the device under FIG. 5, the housing 1 is partitioned into two somewhat equally large chambers K1, K2 by a rigid partition 27. Each chamber features its own inlet opening 2, which is able to close through an air lock 25, 26, and the partition 27 contains its own outlet opening 3 with a funnel 20. In addition, a roll conveyor 6 is provided at each inlet opening. On the top side, each chamber is provided with its own suspended conveyer 5, which corresponds to the suspended conveyer in the structure under FIGS. 3 and 4.

In addition, on an alternating basis, both chambers are connected to a sterilization device 4, which injects (for example) $H_2O_2$ vapor into the chamber.

With the device under FIG. 5 as described above, operating in batches is possible. Thereby, on an alternating basis, the two chambers K1 and K2 are either subjected to sterilization material (wherein, the respective air lock 25, 26 is closed) or, if air lock 25, 26 is opened, loaded with full bags S and the empty bags S are released. For emptying the bags, after a sufficient sterilization time with cyclic operations of the suspended conveyer 5, the bags S are then successively carried, cut open and emptied over the respective funnel 20.

Given the accessibility of the bags S on all sides, the devices described above facilitate intensive treatment and sterilization, such that the feeding of contaminated closures V into the filling system A is reliably prevented. At the same time, in the sterilization device, the area of the suspended conveyer 5 found within the housing 1 is permanently sterilized, while, given the magnetic power transmission, the external propelling area of the suspended conveyer 5 can be housed in the normal environment and, therefore, does not have to be sterilized.

The invention claimed is:

1. Device for feeding sterile closures, which have been delivered in bags, into a filling system for containers comprising a housing that has an inlet opening for the bags, a removal device for the closures, an outlet opening for the closures and a sterilization device, a conveying device provided in the housing to transport the bags wherein the conveying device for the bags is embodied as a suspended conveyer, and wherein the removal device further includes a funnel for the closures falling out of the bags, the funnel being arranged to deposit such closures on a conveyer, the conveyer being closed on all sides and arranged to guide the closures to the filling system.

2. Device according to claim 1, wherein the suspended conveyer successively traverses the sterilization device for the bags, a drying device for the bags and the removal device for the closures.

3. Device according to claim 1 wherein the suspended conveyer comprises an endless track housed within the housing along with runners that are supported, wherein the runners are equipped with seatings for the suspended transportation of the bags.

4. Device according to claim 3, wherein the runners comprise magnets which are also housed outside of the housing and act together as drive magnets.

5. Device according to claim 4, wherein the magnets, which are housed outside of the housing, are housed on an endless link chain, which link chain rotates over two redirecting wheels, wherein one redirecting wheel is able to be driven by a motor.

6. Device according to claim 3, wherein the seatings are one of hooks, pins, or a combination thereof.

7. Device according to claim 1, and wherein two separate sterilization chambers are provided, of which each sterilization chamber exhibits a suspended conveyer, an inlet opening and an outlet opening, wherein the two chambers are able to be connected to a sterilization device on an alternating basis.

8. Device according to claim 7, wherein the two chambers are housed in a common housing with the insertion of a partition.

9. Device according to claim 7, wherein the inlet opening of each chamber is closable through its own air lock.

10. Device according to claim 1, wherein the suspended conveyer overlaps the area of the inlet opening with a roll conveyor for the bags, and within the area of the outlet opening with the funnel for the closures.

11. Method for feeding sterile closures, which have been delivered in bags, into a filling system for containers comprising:
providing a device according to claim 1;
sterilizing a bag using the sterilization device of the provided device;
opening the bag using the removal device of the provided device; and
depositing through the outlet opening of the provided device the closures from the bag on a conveyer, which guides the closures to the filling system.

* * * * *